United States Patent [19]

Laarveld et al.

[11] Patent Number: 5,212,156
[45] Date of Patent: May 18, 1993

[54] SRIF-RELATED PEPTIDES AND USES THEREOF

[75] Inventors: Bernard Laarveld; Roy N. Kirkwood; Philip A. Thacker; Lorraine M. Sordillo; mark Redmond, all of Saskatoon, Canada

[73] Assignee: University of Saskatchewan, Sasakatoon, Canada

[21] Appl. No.: 539,236

[22] Filed: Jun. 18, 1990

Related U.S. Application Data

[63] Continuation-in-part of Ser. No. 369,499, Jun. 22, 1989, abandoned.

[51] Int. Cl.$^5$ ................................................ C07K 7/08
[52] U.S. Cl. ........................................ 514/14; 514/11
[58] Field of Search .................... 530/311; 514/11, 14

[56] References Cited

U.S. PATENT DOCUMENTS

| | | | |
|---|---|---|---|
| 3,842,066 | 10/1974 | McKinley et al. | 530/311 |
| 3,842,067 | 10/1974 | Sarantakis | 530/311 |
| 3,845,204 | 10/1974 | Grant | 530/311 |
| 3,863,008 | 1/1975 | Grant | 514/14 |
| 3,933,784 | 1/1976 | Sarantakis | 514/14 |
| 4,199,500 | 4/1980 | Shields | 530/311 |
| 4,244,947 | 1/1981 | Abraham et al. | 530/311 |
| 4,316,891 | 2/1982 | Guillemin et al. | 530/311 |
| 4,372,884 | 2/1983 | Brown et al. | 530/311 |
| 4,569,926 | 2/1986 | Szabo et al. | 514/14 |
| 4,612,302 | 9/1986 | Szabo et al. | 514/11 |
| 4,812,554 | 3/1989 | Riggs | 530/311 |

FOREIGN PATENT DOCUMENTS

3937539 11/1988 Fed. Rep. of Germany.

OTHER PUBLICATIONS

Feng et al., *Endocrinology* (1987) 120(3):1121-1126.
Bass et al., *J. Endocrinol.* (1987) 112:27-31.
Buonomo et al., *Domestic Animal Endocrinology* (1987) 4(3):191-200.
Dubreuil et al., *Endocrinology* (1989) 125(3):1378-1384.
Laarveld et al., *Can. J. Adnim. Sci.* (1886) 66§77-83.
Morrison et al., *Research in Veterinary Science* (1984) 37:108-113.
Trout et al., *J. Endocrinol.* (1990) 125:123-129.
Vicini et al., *Domestic Animal Endocrinology* (1988) 5(1):35-45.
Grossman et al., *J. Steroid Biochem.* (1984) 21(1):279-286.
Hashimoto et al., *Nihon Univ. J. Med.* (1980) 22:203-211.
Richoux et al., *J. Physiol., Paris* (1981) 77:985-988.
Dubreuil et al., *Endocrinology* (1989) 125(3):1378-1384.
Pui-Domingo et al., *J. Repro. Fertil.* (England) (1988) 82(2):753-759.
Kirkwood et al., *J. Reprod. Immunol.* (Ireland) (1990) 17(3):229-238.
Spencer et al., (1986) *Control and Manipulation of Animal Growth* P. J. Buttery et al., eds., Butterworths, Boston, pp. 279-291.
Schalch et al., *Endogrinology* (1979) 104(4):1143-1151.
Froesch et al., *Proc. Natl. Acad. Sci. USA* (1976) 73(8):2904-2908.

(List continued on next page.)

Arimura et al., *Endocrinology* (1976) 98:540-543.
Tannenbaum et al., *Endocrinology* (1978) 102(6):1909-1914.
Varner et al., *Endocrinology* (1980) 106(3):1027-1032.
Spencer et al., *Livestock Prod. Sci.* (1983) 10:25-37.
Deligeorgia et al., *Animal Production* (1988) 46:304-308.

*Primary Examiner*—Lester L. Lee
*Attorney, Agent, or Firm*—Roberta L. Robins

[57] ABSTRACT

Compositions and methods for modulating SRIF activity as well as enhancing the reproductive performance and immunological function in vertebrates are disclosed. Compositions containing SRIF-related peptides or antibodies thereto can be administered to animals to modulate endogenous SRIF-like activity. The SRIF-related peptides can be linked to a carrier such as ovalbumin, and administered in an Al(OH)$_3$ adjuvant, to enhance the immunogenicity of the SRIF-related peptides.

15 Claims, 6 Drawing Sheets

OTHER PUBLICATIONS

Schusdziarra Somatostatin (1985) Y. C. Patel and G. S. Tannebaum eds. Plenum Publishing Corp., New York, N.Y., pp. 425–445.

Brazeau *Amer. J. Med.* (1986) 81 (Suppl. 68):8–13.

Reichlin, *New Eng. J. of Med.* (1983) 309(24):1495–1501 (part one) and 309(25):1556–1563 (part two).

Hafs et al., *Journal of Animal Science* (1977) 44(6):1061–1066.

Hoefler et al., *Theriogenology* (1988) 29(2):519–524.

Mori et al., *Acta Endocrinologica* (1980) 50(5):969–971.

Watkins et al., *Journal of Clinical Endocrinology* (1980) 50(5):969–971.

Vittoria et al., *Anatl. Histol. Embryol.* (1989) 18:136–142.

Mori et al., *Acta Endocrinologica* (1985) 110:408–412.

Kirkwood et al., *Can. J. Anim. Sci.* (1988) 68:1097–1103.

Kirkwood et al., *Domestic Animal Endocrinology* (1988) 5(4):317–322.

Veldhuis et al., *Biochem. Biophys. Res. Comm.* (1985) 130(1):234–240.

Liebow et al., *Proc. Natl. Acad. Sci.* (1989) 86:2003–2007.

Sutherland, *Science* (1972) 177:401–408.

Tilly et al., *Endocrinology* (1990) 126(4):2079–2087.

Arimura et al., *Endocrinology* (1976) 98:1069–1072.

Moreau et al., *Life Sciences* (1987) 40(5):419–437.

SRIF-RELATED PEPTIDES AND USES THEREOF

CROSS REFERENCE TO RELATED APPLICATION

This is a continuation-in-part application of U.S. Ser. No. 07/369,499, filed Jun. 22, 1989 and now abandoned, which is incorporated herein by reference, and claims priority thereto pursuant to 35 USC 120.

TECHNICAL FIELD

The instant invention relates generally to the field of immunology and more specifically to somatostatin and somatostatin-related peptides and uses thereof.

BACKGROUND

Somatostatin or somatotropin-releasing inhibiting factor (SRIF), is a small peptide hormone that inhibits the release of several endogenous hormones including growth hormone (somatotropin), insulin, and thyroid stimulating hormone (Spencer 1986). These hormones, in turn, regulate the release of still other substances. For example, insulin-like growth factor-1 (IGF-1), formerly referred to as somatomedin, and which mediates the anabolic effects of pituitary growth hormone, appears to be released by the liver only when adequate levels of insulin are present (Schalch et al., 1979). Furthermore, the ability of IGF-1 to stimulate growth may be dependent on thyroid hormones (Froesch et al., 1976). Thus, circulating SRIF levels profoundly affect IGF-1 levels.

SRIF may also influence digestion and absorption of nutrients. Molecules with SRIF-like reactivity increase in plasma following a meal (Schusdziarra, 1985). SRIF also inhibits gastric acid secretion, gall bladder emptying and triglyceride and glucose absorption. Thus, SRIF is involved in regulating nutrient uptake from the gastrointestinal tract.

SRIF may influence the reproductive process through several mechanisms. The literature is clear that SRIF does not have a direct stimulatory or inhibitory effect on pituitary secretion of luteinizing hormone (LH) or follicle stimulating hormone (FSH) (see reviews by Brazeau, 1986; Reichlin, 1983). Several studies in farm animal species have confirmed this. Infusion of SRIF in bulls in vivo failed to change levels of LH in blood (Hafs et al., 1977). Injection of ewes with SRIF failed to change serum LH levels and reproductive efficiency (Hoefler and Hallford, 1988). SRIF may influence the reproductive process through other direct or indirect effects. For example, SRIF is present in porcine ovaries (Mori et al., 1984), in the cytotrophoblast of the immature human placenta (Watkins et al., 1980), and in neuroendocrine cells found in the porcine uterus (Vittoria et al., 1989). SRIF also inhibits meiotic maturation of cultured porcine follicular ova (Mori et al., 1985). Without being bound to a particular theory, it is possible that as a consequence of immunization against SRIF, increased pituitary growth hormone secretion and/or increased nutrient absorption which is independent of growth hormone but directly dependent on SRIF, could occur. In either case this could result in increased levels of IGF-1 and altered reproductive performance. It has also been shown that injection of growth hormone in pigs, which results in increases in IGF-1, leads to increased ovulation rates in gilts in estrous (Kirkwood et al., 1988a,b). Similarly, IGF-1 in cultured swine granulosa cells stimulates steroidogenesis (Veldhuis et al., 1985). Further, SRIF may modulate cellular growth by influencing the extent of phosphorylation of the epidermal growth factor (EGF) receptor, histones, and angiotensin (Liebow et al., 1989). Modulation of the responsiveness of the EGF receptor in granulosa cells may regulate cell development and differentiation (Feng et al., 1987).

Immunization against SRIF may also increase reproductive efficiency by affecting cyclic AMP (cAMP) levels. It is known that SRIF inhibits cAMP activity, however, to the knowledge of the inventors, the action of cAMP in reproductive cells and tissues and on ovulation, has not been previously reported. However, cAMP is known to be an important regulator of several physiological mechanisms and the function of cAMP in controlling hormonal activity has been described (Sutherland, 1972). Without being bound to a particular theory, cAMP may regulate reproductive efficiency as follows. cAMP has been implicated in the function of plasminogen activator (Tilly et al., 1990), a neutral serine protease that catalyzes the conversion of plasminogen to plasmin. Specifically, increases in cAMP levels have been shown to induce plasminogen activator activity in the thecal layer of the largest preovulatory follicle in the hen ovary (Tilly et al., 1990). Plasminogen activator, may in turn, affect several physiological processes within the ovary, including cellular differentiation, follicular maturation and ovulation. SRIF, by inhibiting cAMP, may reduce the effect of the cAMP-stimulating factors, luteinizing hormone, and prostaglandin E, thus reducing the effects of these factors on reproductive performance. Since the regulatory function of cAMP has a long evolutionary history extending back to include bacteria (Stryer, L., 1981), it is likely that agents affecting cAMP levels will be useful in a wide range of organisms.

SRIF may also exert an effect on immunological function. Specifically, it has been postulated that SRIF may inhibit lymphocyte proliferation by blocking both RNA and DNA synthesis, Payan et al., 1984. SRIF also exerts inhibitory effects on mononuclear cells, Yousefi et al., 1990, and inhibits the release of IgA by plasma cells isolated from spleen and Peyer's patches, Stanisz et al., 1986. However, the inventors are unaware of any reports indicating that SRIF directly or indirectly inhibits or stimulates cells of myeloid origin, e.g., polymorphonuclear neutrophilic granulocytes (PMN).

It has been reported that lymphocytes, PMN's and monocytes are capable of synthesizing and secreting small amounts of SRIF, Johnson et al., 1985. The exact role of monocyte-secreted SRIF has not yet been described, although Blalock et al., 1985, suggest that this SRIF may function as a signal transmitter between cells of the immune system.

The mechanism by which antibodies to SRIF enhance PMN activity is not known. However, immunization against SRIF may reduce the potential inhibitory effects that SRIF has on the cells of the immune system. The inhibitory effects may be of two types; one may involve the direct interaction between SRIF and PMNs. Alternatively, SRIF may cause the inhibition of lymphokine release by T-lymphocytes. Lymphokines are produced by activated lymphocytes and enhance leukocyte function. Examples of lymphokines are Interferon α, Interferon γ and Interleukin 2. The reduction of lymphokine secretion caused by SRIF would decrease PMN activity. Therefore, the immunization against SRIF may enhance immunological function since many cells of the immune system are regulated by lymphokines, e.g., PMN's, B lymphocytes, macrophages, monocytes and T lymphocytes.

The phagocytic uptake of bacteria by PMN's is the primary step in the clearance of bacteria and as a result PMNs play a pivotal role in the protection of animals against bacterial infection such as mastitis and bovine respiratory disease. Bacterial infection is particularly prevalent in animals under stress, and/or during the periparturient period, and/or following primary viral infection. Thus, PMN activity is a key factor for the prevention and recovery from bacterial infection in numerous situations.

SRIF is a tetradecapeptide which exists in both linear and cyclic forms. The chemical structure of cyclic SRIF-14 is as follows:

a consistent and measurable immune response against SRIF.

To date, there are no known studies correlating SRIF-like immunomodulation, either active or passive, with reproductive efficiency in animals. U.S. Pat. No. 3,863,008 discloses that increased SRIF levels stimulate luteinizing hormone secretion in vitro, however this effect is not related to an immunological phenomenon. Increased reproductive efficiency in vertebrates would be economically desirable.

DISCLOSURE OF THE INVENTION

The present invention is based on the discovery that immunomodulation of SRIF-like activity enhances both the reproductive efficiency and immunological function of vertebrate subjects. The present invention is also

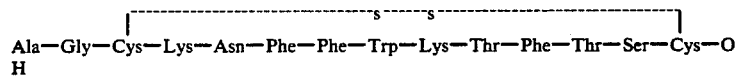

Molecules with SRIF-like activity also exist with sequences extended from the N- and/or C-terminals as well as molecules which contain additions, deletions, or substitutions within the SRIF-14 sequence. Natural forms of SRIF include the following: SRIF-14;, Pro-SRIF, Pro-Pro-SRIF, SRIF-28, SRIF-25, and SRIF-20.

One well-known analog of SRIF is (SRIF) SMS 201-995. A review of such structures is given by Moreau et al. (1987). Other analogs of SRIF are RC-121 and RC-160 (Liebow et al., 1989).

SRIF has been found in all vertebrates studied to date (Spencer, 1986) and is synthesized throughout the body. Thus, levels of SRIF are not easily reduced and studies regarding modulated SRIF concentrations have been limited. However, immunomodulation has provided a method by which one can examine the effects of anti-SRIF activity. This technique utilizes antibodies to SRIF to modulate SRIF-like activity. Antibodies to SRIF can either be administered directly to the subject (passive immunization) or SRIF can be administered in combination with adjuvants and/or carriers so that antibodies are produced in vivo that can modulate SRIF-like activity (active immunization).

SRIF was originally recognized for its inhibitory effect on growth hormone secretion. Its removal from the blood circulation by passive immunization increased growth hormone concentrations in plasma in rats (Arimura and Schally, 1976), and prevented decreases in growth hormone concentration as a result of stress (Arimura et al., 1976) and starvation (Tannenbaum et al., 1978). However, earlier attempts at active immunization to accomplish immunomodulation of SRIF have produced mixed results. For example, removal of SRIF by active immunization has been reported to result in higher plasma growth hormone levels in lambs (Varner et al., 1980; Spencer et al., 1983a). This, however, resulted in inconclusive effects on growth. Spencer et al. (1983a,b) observed increased growth with improved feed efficiency in lambs immunized against SRIF, whereas Varner et al. (1980) reported a significantly lower growth rate. Furthermore, active immunization against SRIF failed to increase either milk production or growth rates in sheep (Deligeorgis et al., 1988). The often contradictory findings reported in the above references may be explained by the difficulty in obtaining based on the discovery of a highly effective, novel, vaccine composition for modulating endogenous SRIF levels. Such a composition finds use not only in enhancing reproductive efficiency, but also in regulating various other physiological functions related to SRIF, as described in the Background. Immunomodulation of SRIF can be accomplished using either active or passive immunization.

In one embodiment, the present invention is directed to a composition for enhancing the reproductive efficiency in a vertebrate subject by inducing an immunologic reaction. The composition includes a pharmaceutically acceptable vehicle and an SRIF-related peptide.

In other embodiments, the instant invention is directed to a composition for enhancing immunological function in a vertebrate subject by modulating SRIF activity as well as a composition for enhancing phagocytic cell function. The compositions include a pharmaceutically acceptable vehicle and SRIF-related peptides.

In still further embodiments, compositions including antibodies against molecules with SRIF-like activity in a pharmaceutically acceptable vehicle are disclosed.

In other embodiments, the present invention is directed to methods for modulating SRIF activity in a vertebrate subject, enhancing the reproductive efficiency in a vertebrate subject, and enhancing phagocytic cell function in a vertebrate subject, by inducing an immunologic reaction. The methods comprise administering to the vertebrates a composition comprising a pharmaceutically acceptable vehicle and a therapeutically effective amount of a SRIF-related peptide. In particularly preferred embodiments, the SRIF-related peptide is SRIF-14 linked to a carrier.

In other embodiments, the instant invention is directed to methods for enhancing the reproductive efficiency in vertebrates and enhancing phagocytic cell activity, by inducing an immunologic reaction, comprising administering to the vertebrates compositions including a pharmaceutically acceptable vehicle and antibodies against SRIF-like activity in an amount sufficient to modulate SRIF-like activity in the vertebrates These and other embodiments of the present invention will readily occur to those of ordinary skill in the art in view of the disclosure herein.

DETAILED DESCRIPTION

Figure 1:
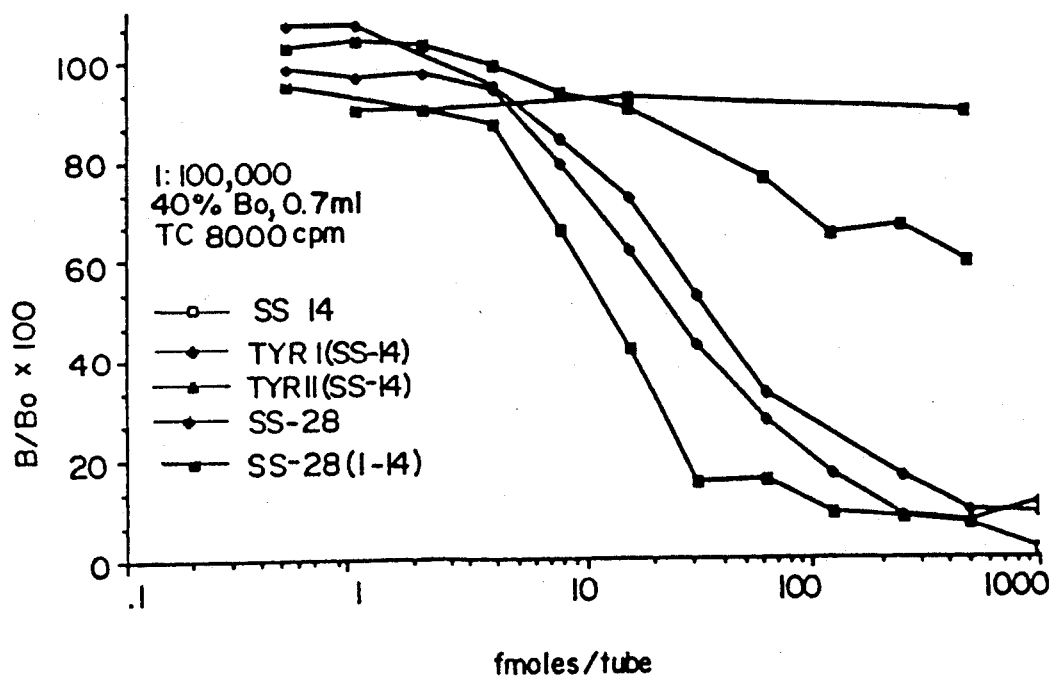
FIG. 1 depicts the cross-reaction profile of antiserum raised in sheep no. 1228 against SRIF-14 with SRIF-related peptides.

The practice of the present invention will employ, unless otherwise indicated, conventional techniques of immunology, protein chemistry, biochemistry and molecular biology, which are within the skill of the art. Such techniques are explained fully in the literature. See, e.g., *Handbook of Experimental Immunology*, Vols. I-IV (D. M. Weir and C. C. Blackwell eds., 1986, Blackwell Scientific Publications), the series, *Methods in Enzymology* (S. Colowick and N. Kaplan eds., Academic Press, Inc.).

A. Definitions

In describing the present invention, the following terms will be employed, and are intended to be defined as indicated below.

By "vertebrate" is meant any animal having a functional immune system, and includes without limitation birds, such as chickens, turkeys, quail, game hens, parrots, and the like; fish; and mammals such as humans, cattle, pigs, horses, dogs, cats, sheep, elephants, and other domestic or wild animals.

"Enhancing reproductive efficiency" is defined as any improvement of reproductive or breeding performance in vertebrates. Such improvement includes, but is not limited to, improved ovulation rates, conception rates, increased incidence of estrous, estrus, improved fertility in both males and females, improved litter sizes, increased survival of ova or embryos, and increased number of offspring. Also included in this definition is the treatment of reproductive inefficiency due to such factors as anestrous, repeat breeding, infertility, and abortion.

"Enhancing immunological function" is defined as any improvement of immunological performance in vertebrates. Such improvements include, but are not limited to, improved leukocyte activity, increased antibody secretion, increased lymphokine secretion, increased cytokine secretion and improved resistance to disease.

By "enhanced phagocytic cell function" is meant any improvement of immunological performance in vertebrates particularly relating to PMN function. Such improvement in PMN function includes, but is not limited to, increased superoxide production, increased chemotaxis and decreased migration. Improvement of PMN function affords protection against a wide variety of organisms, including, but not limited to, *Escherichia coli, Staphylococcus aureus. Streptococcus agalactiae, Streptococcus uberis, Corynebacterium bovis, Pasteurella hemolytica*. Vertebrates are particularly susceptible to these organisms under conditions of stress, following viral infection, and during the periparturient period. For example, mastitis is one of several diseases attributable to such bacterial infection.

By "somatostatin" or "SRIF" is meant any molecule with SRIF-like activity including molecules with sequences extended from the N- and/or C-termini of SRIF-14 as well as molecules containing additions, deletions, or substitutions to the SRIF-14 sequence. Any of the above may be in a linear or cyclic form. Examples of these peptides include, but are not limited to, SRIF-14, either cyclic or linear, [Tyr$^1$]-SRIF-14, [Tyr$^{11}$]-SRIF-14, SRIF-25 and SRIF-28 (either cyclic or linear).

By "an SRIF-related peptide" is meant any protein, polypeptide, or peptide which displays SRIF immunoreactivity. Also encompassed by the term are structural analogs of SRIF which exhibit SRIF receptor binding activity such that other SRIF-related peptides are prevented from binding the SRIF receptor. Such a substance will cross-react with antibodies raised against SRIF-14, either cyclic or linear.

A "rotavirus VP6 protein" refers to the art-recognized major viral protein of the inner capsid from any species or strain within the family Reoviridae. See, e.g., Kapikian et al., 1985. Examples of rotavirus strains from which the VP6 protein can be isolated and employed in the present invention include, but are not limited to, Simian SA-11, human D rotavirus, bovine UK rotavirus, human Wa or W rotavirus, human DS-1 rotavirus, rhesus rotavirus, the "0" agent, bovine NCDV rotavirus, human S2 rotavirus, human KUN rotavirus, human 390 rotavirus, human P rotavirus, human M rotavirus, human Walk 57/14 rotavirus, human Mo rotavirus, human Ito rotavirus, human Nemoto rotavirus, human YO rotavirus, human McM2 rotavirus, rhesus monkey MMU18006 rotavirus, canine CU-1 rotavirus, feline Taka rotavirus, equine H-2 rotavirus, human St. Thomas No. 3 and No. 4 rotaviruses, human Hosokawa rotavirus, human Hochi rotavirus, porcine SB-2 rotavirus, porcine Gottfried rotavirus, porcine SB-1A rotavirus, porcine OSU rotavirus, equine H-1 rotavirus, chicken Ch.2 rotavirus, turkey Ty.1 rotavirus, bovine C486 rotavirus, and strains derived from them. Thus the present invention encompasses the use of VP6 from any rotavirus strain, whether from subgroup I, subgroup II, or any as yet unidentified subgroup, as well as from any of the serotypes 1-7, as well as any as yet unidentified serotypes. Such VP6 proteins can be used as immunologic carriers of polypeptides. These carrier molecules comprise amino acid sequences of rotavirus VP6 amino acid sequences which are unique to the class, or any member of the class, of VP6 polypeptides. Such unique sequences of VP6 proteins are referred to as a "rotavirus VP6 inner capsid protein amino acid sequence."

A carrier that is "substantially homologous to a rotavirus VP6 inner capsid protein or a functional fragment thereof" is one in which at least about 85%, preferably at least about 90%, and most preferably at least about 95%, of the amino acids match over a defined length of the molecule. A "functional fragment" of a rotavirus VP6 inner capsid protein is a fragment with the capability of acting as a carrier molecule for SRIF-related peptides as defined above.

By "modulating SRIF or SRIF-like activity" is meant changing the endogenous levels of SRIF or SRIF-related peptides, so that the desired effect, such as an improvement in reproductive efficiency or enhancement in nonspecific immunity, is achieved. The change in endogenous SRIF levels occurs due to the administration of the subject peptides and antibodies thereto. Normally, the effect of these peptides and antibodies will be to lower endogenous SRIF levels.

The term "therapeutically effective amount" refers to the amount of a SRIF-related peptide or of anti-SRIF antibody sufficient to modulate endogenous SRIF-like activity in a recipient subject when administered in the composition of the invention.

By "immunologic reaction" is meant the development in a vertebrae of either a cell- or antibody-mediated immune response to the peptide of interest. Usually, such a response consists of the vertebrate producing antibodies and/or cytotoxic T cells directed specifically to the peptide of interest.

B. General Methods

Central to the instant invention is the discovery that SRIF-related peptides can alter reproductive performance in normal vertebrates and invertebrates with reproductive abnormalities. These substances can be used in a composition administered to such vertebrates, either alone or in combination, with advantageous results. Also important, is the discovery of novel compositions, highly effective in modulating SRIF levels and enhancing phagocytic cell function.

Useful in the subject methods and compositions are molecules which have SRIF-like activity, and analogs thereof. Such molecules are available commercially and can be obtained in any of several forms and include but are not limited to SRIF-14, SRIF-28, SRIF-25, SRIF-20, RC-121, RC-160, and SMS-201-995 in either cyclic or linear forms.

Because SRIF and related compounds are relatively small, they can readily be produced by chemical synthesis such as by solid phase peptide synthesis, using known amino acid sequences. Such methods are known to those skilled in the art. The materials used in the present disclosure were synthesized by Bachem Inc. (Torrance, Calif.). SRIF-related peptides can also be made by recombinant DNA methods known in the art.

SRIF or other substances exhibiting SRIF immunoreactivity, can be administered to vertebrates to stimulate the active development of an immune response. They can also be used to produce antibodies, both polyclonal and monoclonal. These antibodies, in turn, can be administered to a vertebrate to modulate endogenous SRIF so that reproductive abilities and nonspecific immunity of the recipient subjects can be enhanced.

If polyclonal antibodies are desired, a selected mammal, (e.g., mouse, rabbit, goat, horse, etc.) is immunized with SRIF, preferably SRIF-14, or an immunogenic fragment thereof, or a mutated form. Serum from the immunized animal is collected and treated according to known procedures. If serum containing polyclonal antibodies to the protein of interest contains antibodies to other antigens, the polyclonal antibodies can be purified by immunoaffinity chromatography, using known procedures.

Monoclonal antibodies to the proteins of the present invention, and to the fragments thereof, can also be readily produced by one skilled in the art. The general methodology for making monoclonal antibodies by hybridomas is well known. Immortal antibody-producing cell lines can be created by cell fusion, and also by other techniques such as direct transformation of B lymphocytes with oncogenic DNA, or transfection with Epstein-Barr virus. See, e.g., M. Schreier et al., *Hybridoma Techniques* (1980); Hammerling et al., *Monoclonal Antibodies and T-cell Hybridomas* (1981); Kennett et al., *Monoclonal Antibodies* (1980); see also U.S. Pat. Nos. 4,341,761; 4,399,121; 4,427,783; 4,444,887; 4,452,570; 4,466,917; 4,472,500; 4,491,632; and 4,493,890. Panels of monoclonal antibodies produced against SRIF, or fragment thereof, can be screened for various properties; i.e., for isotype, epitope, affinity, etc.

Animals can be immunized with the compositions of the present invention by administration of the proteins of interest, or a fragment thereof, or an analog thereof, or antibodies thereto. If a fragment or analog is used, it will include the amino acid sequence of the epitope which interacts with the immune system to immunize the animal to that and structurally similar epitopes.

The immunogenicity of the SRIF-related peptides can be increased prior to immunization by linking to a carrier. Suitable carriers are typically large, slowly metabolized macromolecules such as: proteins; polysaccharides, such as sepharose, agarose, cellulose, cellulose beads and the like; polymeric amino acids such as polyglutamic acid, polylysine, and the like; amino acid co-polymers; muramyl dipeptide or other bacterial cell wall components; and inactive virus particles. Especially useful protein substrates are serum albumins such as BSA or ovalbumin, keyhole limpet hemocyanin, immunoglobulin molecules, thyroglobulin, and other proteins well known to those skilled in the art.

The protein substrates may be used in their native form or their functional group content may be modified by, for example, succinylation of lysine residues or reaction with Cys-thiolactone. A sulfhydryl group may also be incorporated into the carrier (or antigen) by, for example, reaction of amino functions with 2-iminothiolane or the N-hydroxysuccinimide ester of 3-(4-dithiopyridyl propionate. Suitable carriers may also be modified to incorporate spacer arms (such as hexamethylene diamine or other bifunctional molecules of similar size) for attachment of peptides.

Particularly suitable carriers for use in the present invention are the VP6 polypeptides of rotaviruses, or functional fragments thereof, as disclosed in commonly owned U.S. patent application Ser. No. 092,120, filed on Sep. 2, 1987 and incorporated herein by reference. Also useful is a fusion product of a viral protein and the epitope of interest made by methods disclosed in U.S. Pat. No. 4,722,840. Still other suitable carriers include a particulate antigen presentation system as disclosed in PCT Application No. GB87/00764, as well as cells, such as lymphocytes. Presentation in this form mimics the natural mode of presentation in the subject, which gives rise to the immunized state. Alternatively, the proteins of the present invention may be coupled to erythrocytes, preferably the subject's own erythrocytes. Methods of coupling peptides to proteins or cells are known to those of skill in the art.

The proteins and antibodies of the present invention are preferably mixed with a pharmaceutically acceptable vehicle or excipient prior to use. Typically, the compositions are prepared as injectables, preferably for intramuscular and/or subcutaneous injection, either as liquid solutions or suspensions. Solid forms suitable for solution in, or suspension in, liquid vehicles prior to injection may also be prepared. The preparation may also be emulsified or the active ingredient encapsulated in liposome vehicles or expressed on the exterior of liposome vehicles by anchoring in the liposomal membrane. The active immunogenic ingredient is often mixed with vehicles containing excipients which are pharmaceutically acceptable and compatible with the active ingredient. Suitable vehicles are, for example, water, saline, dextrose, glycerol, ethanol, or the like, and combinations thereof. In addition, if desired, the vehicle may contain auxiliary substances such as wetting or emulsifying agents, pH buffering agents, or adjuvants which enhance the effectiveness of the vaccine. Adjuvants may include for example, muramyl dipeptides, avridine, aluminum hydroxide, oils, saponins and other substances known in the art. Actual methods of preparing such dosage forms are known, or will be apparent, to those skilled in the art. See, e.g., Remington's Pharmaceutical Sciences, Mack Publishing Company, Easton, Pa., 15th edition, 1975.

It has been found that a particularly useful formulation for modulating SRIF activity includes an ovalbumin-linked SRIF or SRIF-related peptide, in combination with 25%-30% $Al(OH)_3$ as an adjuvant.

The composition or formulation to be administered will contain a quantity of the SRIF-related peptide or antibodies thereto, adequate to modulate endogenous SRIF in the vertebrate being treated, the exact amount being readily determined by one skilled in the art. The active ingredient will typically range from about 1% to about 95% (w/w) of the composition, or even higher or lower if appropriate. The quantity to be administered depends on the animal to be treated and the capacity of the animal's immune system to modulate SRIF-like activity. It has been found that in the present formulations, 125 μg of active ingredient per ml of injected solution is adequate to raise an immunological response when a dose of 2 to 4 ml per animal is administered. Other effective dosages can be readily established by one of ordinary skill in the art through routine trials establishing dose response curves. The animal is immunized by administration of SRIF-related peptide or an immunogenic fragment thereof, or analog thereof, in at least one dose, and preferably more than one dose. The animal may be administered as many doses as is required to maintain a state whereby SRIF-like activity is modulated to a sufficient level to exert a biological effect.

Additional formulations which are suitable for other modes of administration include suppositories and, in some cases, aerosol, intranasal and oral formulations. For suppositories, the vehicle composition will include traditional binders and carriers, such as, polyalkaline glycols, or triglycerides. Such suppositories may be formed from mixtures containing the active ingredient in the range of about 0.5% to about 10% (w/w), preferably about 1% to about 2%. Oral vehicles include such normally employed excipients as, for example, pharmaceutical grades of mannitol, lactose, starch, magnesium stearate, sodium saccharin cellulose, magnesium carbonate, and the like. These oral compositions may be taken in the form of solutions, suspensions, tablets, pills, capsules, sustained release formulations, or powders, and contain from about 10% to about 95% of the active ingredient, preferably about 25% to about 70%.

Intranasal formulations will usually include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

Furthermore, the subject SRIF peptides may be formulated into the subject compositions in either neutral or salt forms. Pharmaceutically acceptable salts include the acid addition salts (formed with the free amino groups of the active polypeptides) and which are formed with inorganic acids such as, for example, hydrochloric or phosphoric acids, or such organic acids as acetic, oxalic, tartaric, mandelic, and the like. Salts formed from free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Below are examples of specific embodiments for carrying out the present invention. The examples are offered for illustrative purposes only, and are not intended to limit the scope of the present invention in any way.

C. Experimental

Materials and Methods

SRIF 14 (cyclic) (SS-14), [$Tyr^1$]-SRIF, [$Tyr^{11}$]-SRIF, SRIF 28 (cyclic) (SS-28) and SRIF 28 (1-14) (SS-28 (1-14)) were purchased from Bachem Inc., Torrance, Calif. Carbodiimide (1-ethyl-3-(3-dimethylaminopropyl) carbodiimide HCl; Pierce) and ovalbumin (99% pure; Sigma) were used as conjugation agent and as carrier, respectively. Freund's Complete and Incomplete Adjuvants were from a commercial source (Sigma or Difco). $Al(OH)^3$-alhydrogel was from Superfos (Denmark).

Cross-bred sheep were maintained at the University of Saskatchewan Sheep Research Unit according to normal commercial management practice. The sheep flock was managed intensively for reproductive purposes. The ewes were bred every 8 months resulting in 3 lambings every 2 years. This results in one breeding out of season (May-June), with the remaining breedings in January or September. Estrous was synchronized using intravaginal sponges impregnated with medroxyprogesterone acetate (60 mg). Estrous was induced by photoperiod manipulation for out of season breeding. Rams were semen tested twice a year and introduced at a ratio of 1 ram to 10 ewes after sponge removal and left for 25 days. The immunized ewes and their contemporaries (controls) were managed as one group. Nutritional management of the ewes and rams was according to normal practice, including flushing of ewes prior to breeding.

All experimentation with swine was conducted at the Prairie Swine Center, University of Saskatchewan. The swine herd was maintained according to normal commercial practice, including natural breeding of gilts and sows.

EXAMPLE 1

Preparation of Immunogenic Compositions

SRIF-14 was conjugated to ovalbumin using carbodiimide in the following manner.

106 mg of SRIF-14 was dissolved in 26.5 ml distilled water (dw);
424 mg ovalbumin in 50 ml dw, and;
742 mg carbodiimide in 22 ml dw.

The carbodiimide solution was mixed with the ovalbumin solution. The SRIF solution was added dropwise over a 10-minute period under continuous stirring at room temperature. The reaction was allowed to continue for 24 hours under continuous stirring at room temperature in the dark. Upon completion, the reaction mixture was dialyzed against dw (1:20) at 4° C. for 48 hours with water changes every 12 hours. The molecular weight cut-off of the dialysis tubing was 3000. The efficiency of conjugation of SRIF to ovalbumin was determined by inclusion of $^{125}$I-[Tyr$^1$]-SRIF-14. Efficiencies for several reactions ranged from 55–60%. It was estimated that the molar ratio of SRIF to ovalbumin was 3:1. The final preparation was emulsified in a double volume of Freund's Complete Adjuvant.

Figure 7:
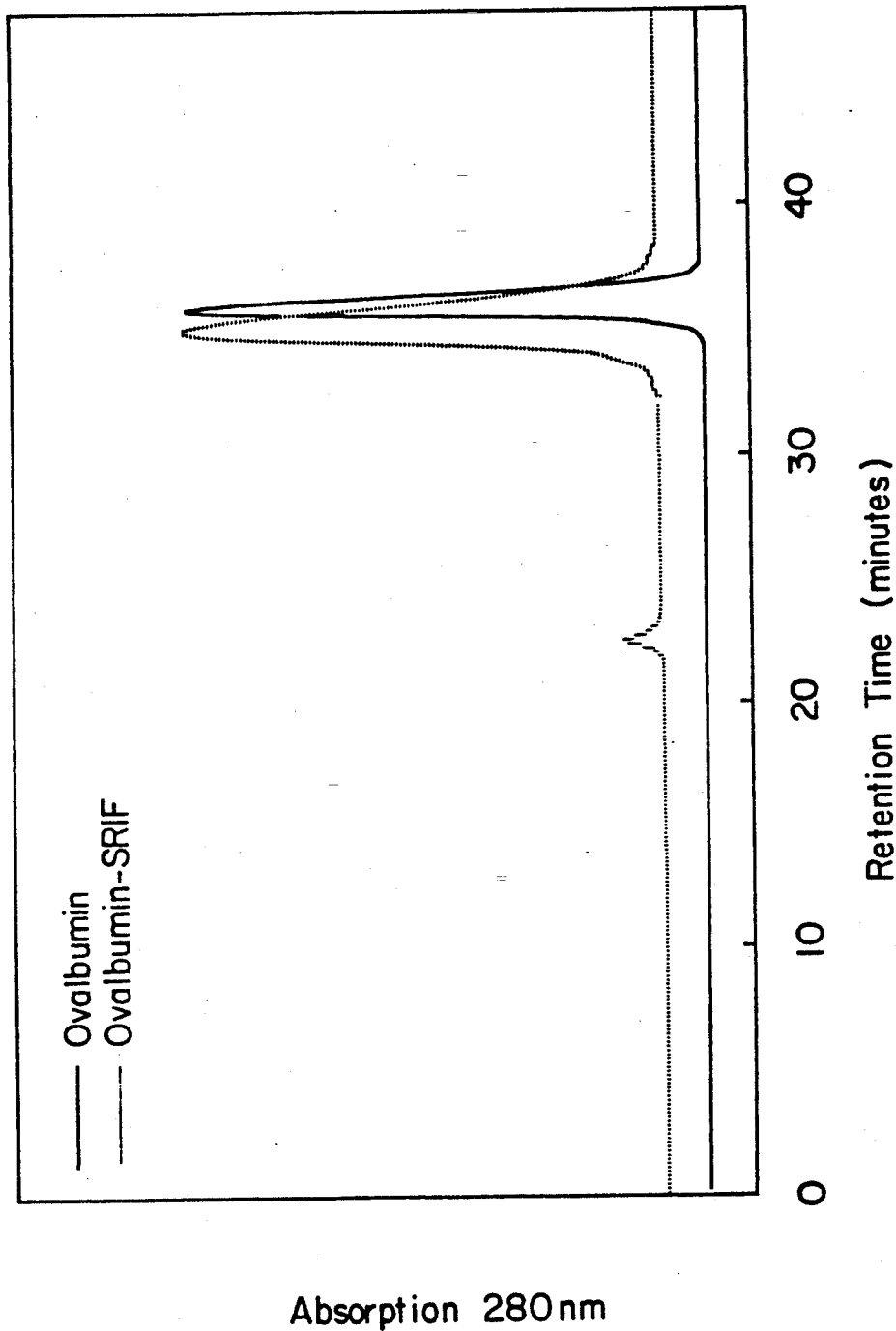
FIG. 7 depicts a reversed phase HPLC chromatogram of ovalbumin carrier alone (solid lines) and ovalbumin carrier conjugated to SRIF (dotted lines).

Surprisingly, when the SRIF-ovalbumin preparation was analyzed by reversed phase high pressure liquid chromatography, the chromatogram (FIG. 7) indicated that the conjugate was composed of several molecules of SRIF coupled to a single ovalbumin molecule. High molecular weight aggregates of ovalbumin were not observed. This is unusual for a preparation produced through a chemical linkage process, such as carbodiimide, since large cross-linked aggregates of carrier molecules are often produced. The described method of conjugation results in an extremely effective immunogenic preparation, which upon inoculation into vertebrates elicits a neutralizing antibody response, as exemplified below.

EXAMPLE 2

Measurement of Antibody Titers Against SRIF

Antibody titers against SRIF in blood were determined by a liquid phase direct binding assay with $^{125}$I-[Tyr$^1$]-SRIF-14 and separation of bound/unbound ligand by charcoal extraction (Laarveld et al., 1986). The titer reported is the final dilution of plasma required to obtain 50% binding of 8000 cpm of monoiodinated [Tyr$^1$]-SRIF-14 (approximately 1.8 pg). In some cases reference is made to a titer in terms of a final dilution required to obtain 35% binding.

EXAMPLE 3

Preparation of Antisera for the Passive Immunization of Animals Against SRIF Sheep were hyperimmunized against the immunogenic preparation from Example 1. Two weeks after immunization, 500 ml volumes of blood were obtained by sampling from the jugular vein. The blood was allowed to clot, and then centrifuged to separate the serum from the cells. The serum from the animals was either employed directly or the antibodies further purified from the serum using either conventional techniques, e.g., $(NH_4)_2SO_4$ precipitation, or affinity chromatography using protein A Sepharose or protein G Sepharose. These methods are familiar to those skilled in the art and are described in Harlow and Lane (1988).

EXAMPLE 4

Measurement of Cross-reaction of Polyclonal Antisera With Various SRIF-like or SRIF-related Peptides Characterization of the antisera raised with the immunogen from Example 1 was carried out for a limited number of sheep. In a normal radioimmunoassay procedure an appropriate dilution of antiserum in phosphate buffered saline (PBS) to provide limited binding of the radioactive tracer $^{125}$I-[Tyr$^1$]-SRIF-14 (6000–8000 cpm), was incubated with serial dilution of the following peptides: SRIF-14, [Tyr$^1$]-SRIF-14, [Tyr$^{11}$]-SRIF-14, SRIF-28, SRIF-28(1-14). The displacement of the radioactive tracer (B/Bo ×100; % binding) was followed.

Figure 2:
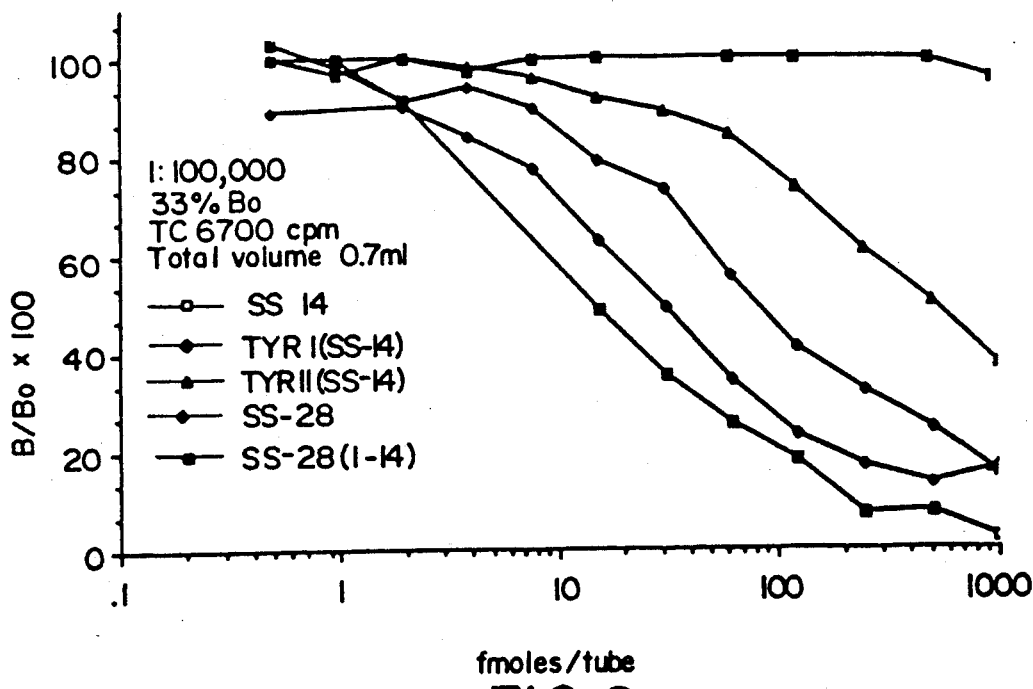
FIG. 2 shows a cross-reaction profile of antiserum raised in sheep no. 1277 against SRIF-14 SRIF-related peptides.
Figure 3:
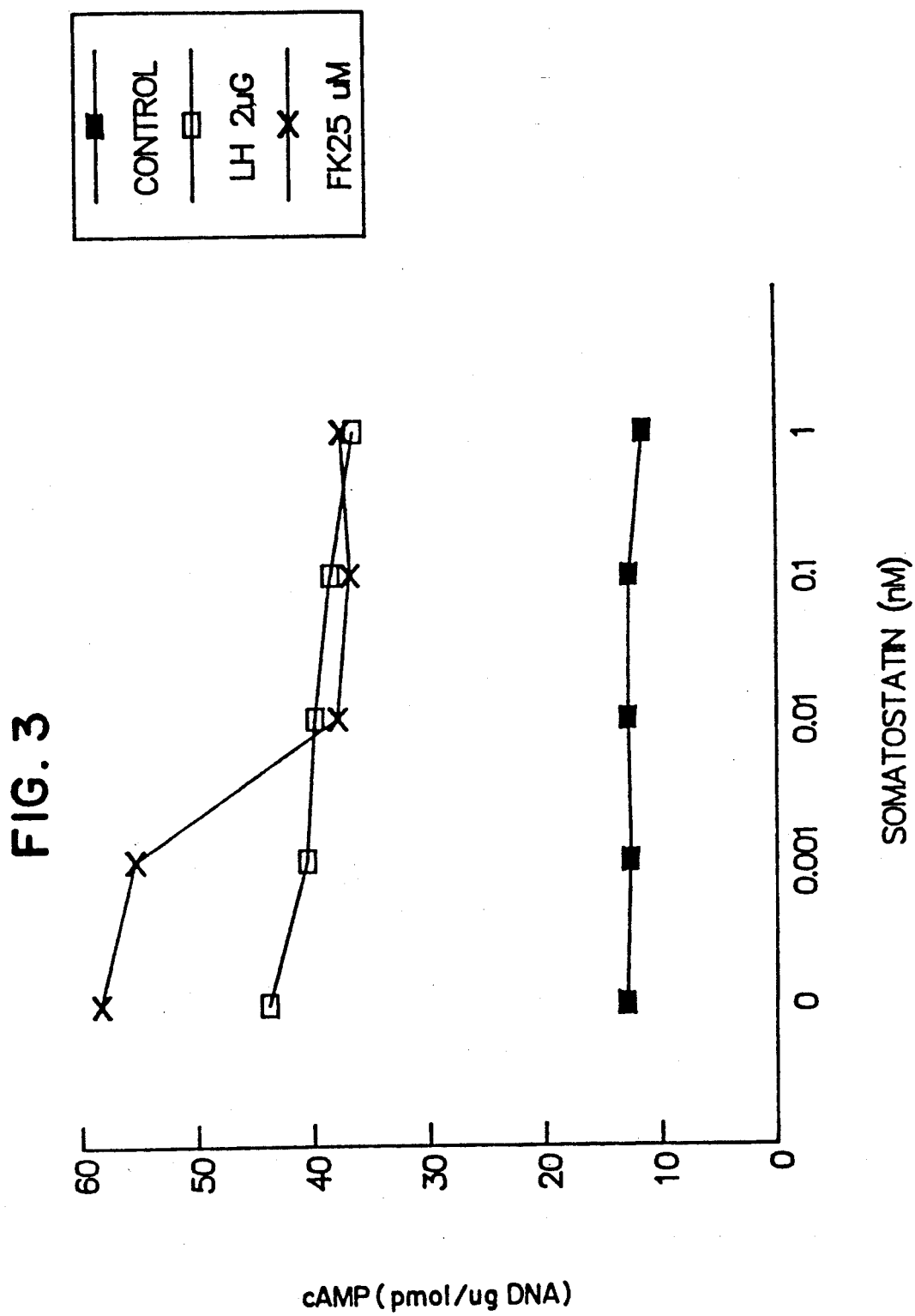
FIG. 3 shows the inhibitory relationship between SRIF and cAMP levels in granulosa cells isolated from mature ovarian follicles. Test cells were incubated in the presence of luteinizing hormone (LH) or forskolin (FK).
Figure 4:
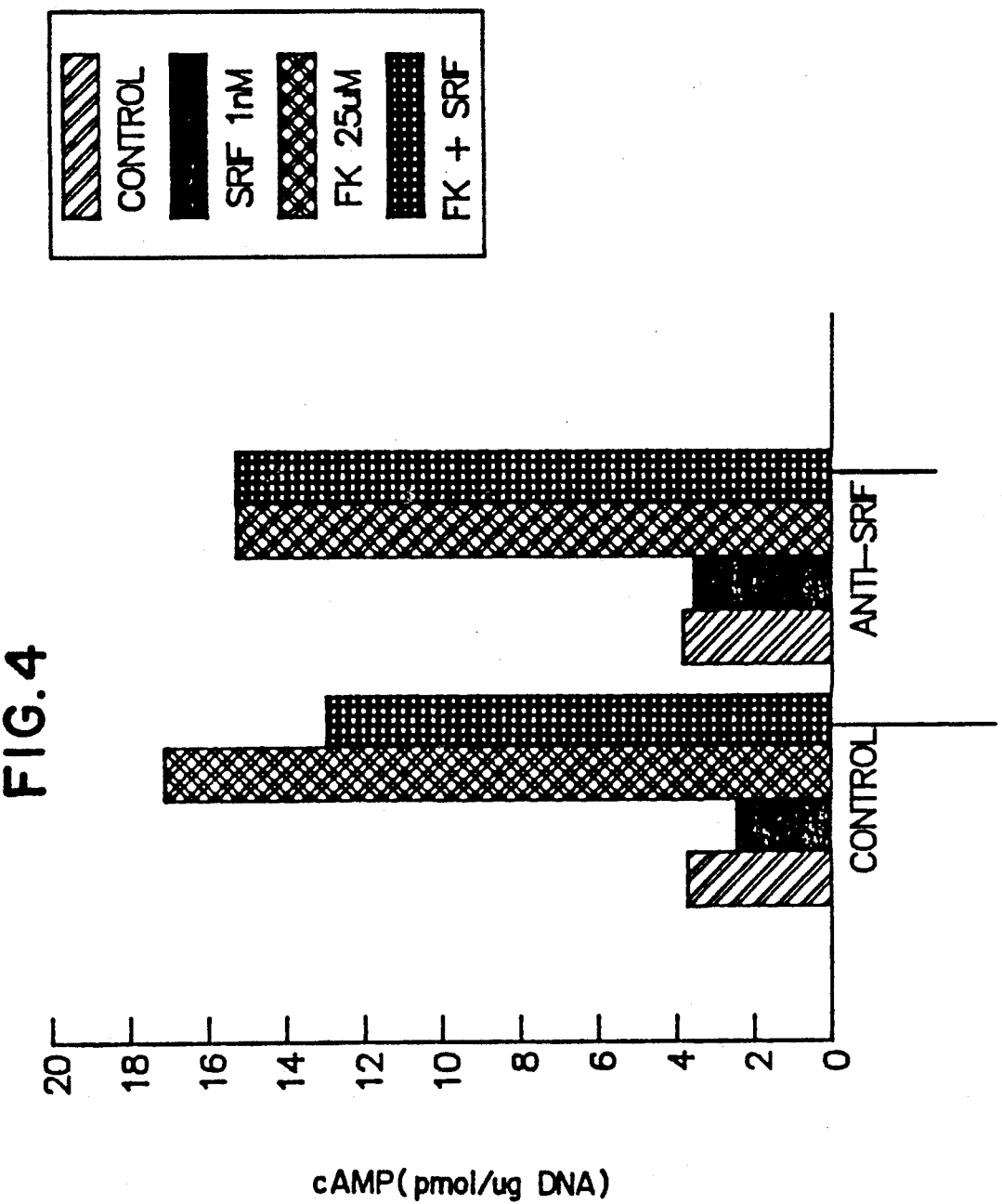
FIG. 4 depicts cAMP levels in granulosa cells isolated from mature ovarian follicles. Test cells were incubated with FK either in the presence or absence of SRIF, as well as in the presence or absence of antibody against SRIF.
Figure 5:
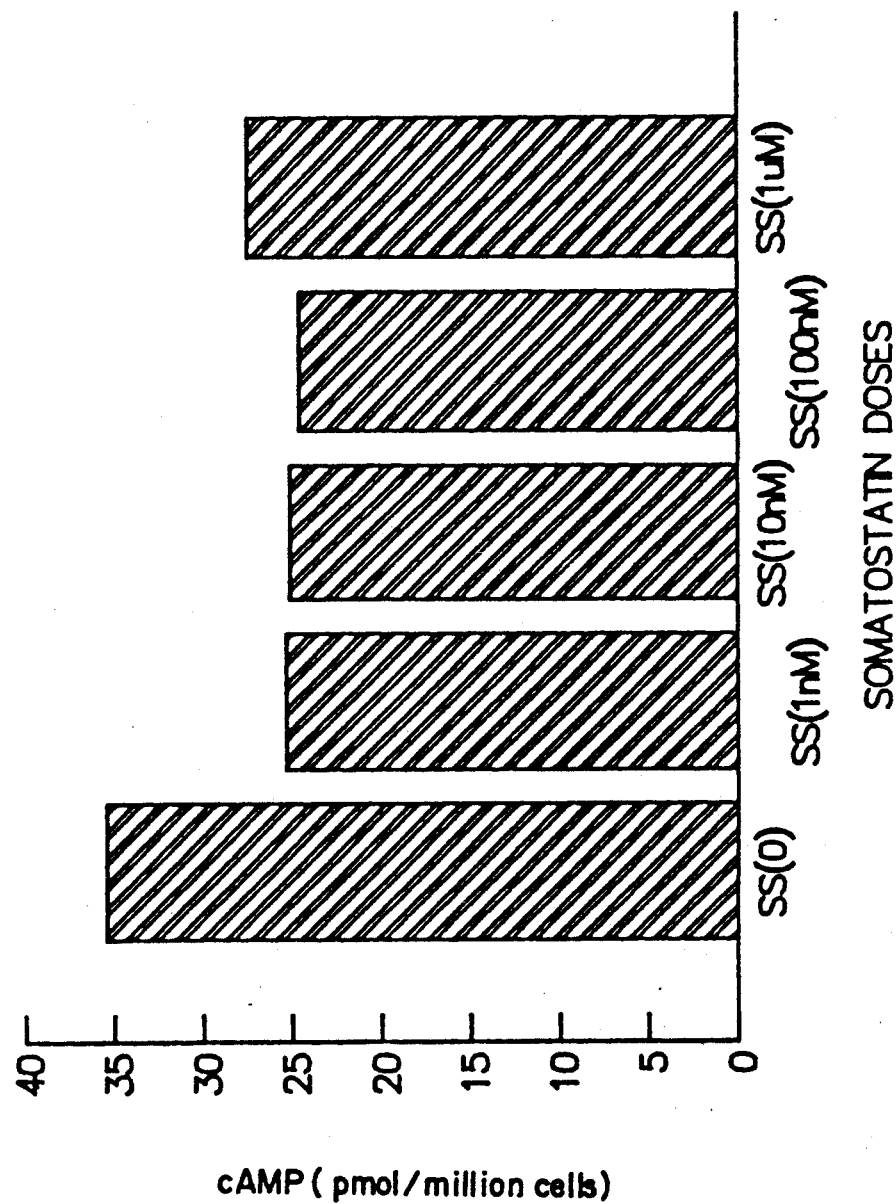
FIG. 5 shows the inhibitory effect of SRIF on basal cAMP levels in pig luteal cells.

The SRIF-ovalbumin conjugate induced production of polyclonal antisera which cross-reacted with SRIF-14, SRIF-28, and [Tyr$^1$]-SRIF-14. Cross-reaction with [Tyr$^{11}$]-SRIF-14 was considerably lower, while no cross-reaction occurred with SRIF-28 (1-14). Examples of two cross reaction tests of sheep antisera can be seen in FIGS. 1 and 2. The results indicate a common cross reaction pattern (Patel 1984) and that the primary epitope of SRIF lies in the ring, since substitution with tyrosine at position 11 resulted in a major loss of activity.

EXAMPLE 5

Breeding Performance of Sheep Immunized Against SRIF

The immunogenic preparation from Example 1 was injected subcutaneously into sheep and intramuscularly into gilts at two sites in the neck region. Dosages were in the range of 0.25 to 0.50 mg SRIF-14 per animal, which gave a dose of from 5 to 15 µg/kg. Booster immunizations, using the same doses and injected into the neck region, were given using Freund's Incomplete Adjuvant. Boosters were given after 3 weeks and then at 4-week intervals, or as necessary. Animals always received a booster vaccination 10 days prior to breeding. Titers against SRIF in the ewes covered a wide range from $10^4$ to $3 \times 10^5$ (reciprocals).

Breeding performance of sheep during in season breeding was enhanced by immunization against SRIF (Table 1). Conception rate upon first service was increased (P<0.05) by 15% and overall conception rate was increased (P<0.01) by 15%. Immunized ewes had a 100% conception rate.

TABLE 1

Effect of Immunization Against SRIF on Breeding Performance of Ewes During Fall and Winter[1]

| | Control | SRIF-immune |
|---|---|---|
| Number of Observations | 89 | 48 |
| First service: | | |
| number conceived | 55 | 37 |
| conception rate | 61.8% | 77.1%* |
| Second service: | | |
| number conceived | 21 | 11 |
| conception rate | 23.6% | 22.9% |
| Number open | 13 | 0 |
| Overall conception rate | 85.4% | 100%** |
| Lambs per birth | 2.05 | 2.06 |
| Anti-SRIF-14 titers[2] | — | $10^4$ to $3 \times 10^5$ |

[1] September and January.
[2] Range of reciprocal titers.
*Means are significantly different (P < 0.05); Fisher's Exact Test.
**Means are significantly different (P < 0.01).

Out of season breeding generally results in poorer breeding performance (Rawlings et al., 1987). However, in this case immunization against SRIF also enhanced (P<0.05) overall conception rate from 30.8% in controls to 70.8% in immunized animals (Table 2).

TABLE 2

Effect of Immunization Against SRIF on Breeding Performance of Ewes During Out of Season Breeding[1,2]

|  | Control | SRIF-immune |
|---|---|---|
| Number of Observations | 13 | 24 |
| First service: |  |  |
| number conceived | 4 | 15 |
| conception rate | 30.8% | 62.5%[7] |
| Overall conception rate after two services: |  |  |
| number conceived | 4 | 17 |
| conception rate | 30.8% | 70.85%* |
| Anti-SRIF-14 titers[3] | — | $10^4$ to $5 \times 10^4$ |

[1]Breeding in June.
[2]Photoperiod managed to simulate fall day length.
[3]Range of reciprocal titers.
[7]P = 0.066; Fisher's Exact Test.
*P = 0.022

EXAMPLE 6

Out of Season Breeding Performance of Sheep Immunized Against SRIF

The immunogenic preparation of Example 1, in an adjuvant of 25% Al(OH)$_3$ alhydrogel instead of Freund's adjuvant, was injected intramuscularly into sheep at the semitendinosus/semimembranosus site. The dosage used was 100 µg of conjugated SRIF-14 per animal. Two booster immunizations, using the same dose and injected into the same site, were administered at three and five weeks post primary immunization, respectively. The final injection was given approximately 7 days prior to breeding. The breeding performance was monitored by visual inspection of the animals and by identifying marker patterns on the ewes backs which resulted from mounting by a ram bearing a crayon marker harness. These observations were made first thing in the morning and then periodically during the day.

The out-of-season breeding performance of sheep was enhanced by immunization against SRIF (see Table 3). The results of this trial are indicative of an increased incidence of estrus, which corroborates the increased conception rates found in the other examples.

TABLE 3

| | Out of Season Breeding Performance | | |
|---|---|---|---|
| Group | No. of Animals | No. of Animals Marked | % animals bred |
| Immunized | 31 | 22 | 71 |
| Control | 28 | 13 | 46 |

EXAMPLE 7

Breeding Performance of Swine Immunized Against SRIF

Gilts received their primary immunization against SRIF at a body weight of 35-45 kg and the secondary immunization 21 days later. The dosage administered ranged from 5 to 15 µ/kg. At a weight of 95 kg, gilts were estrous induced with PMSG (500 IU) (Kirkwood et al, 1988) and given a booster immunization 7 days later. The gilts were bred naturally upon first observed natural estrus and, if necessary, the gilts were allowed a second estrous cycle followed by natural breeding. Immunized gilts were compared to contemporaries selected at the time of primary immunization.

Two studies were performed using these gilts. A number of immunized and control gilts were slaughtered following their first natural estrus to determine ovulation rate. In the second study the gilts were bred as described and allowed to farrow.

As can be seen in Table 4, immunization against SRIF 17 improved the ovulation rate (P<0.10) in gilts.

TABLE 4

Ovulation Rate Upon First Natural Estrus of Gilts Immunized Against SRIF and of Control Gilts

| | Control | SRIF-immune[1] | P |
|---|---|---|---|
| Number of Observations | 17 | 15 | |
| Ovulation rate | 10.7 ± 0.4[1] | 11.8 ± 0.6 | 0.096[2] |
| Anti-SRIF-14 titers[3] | 0 | 3800 | |

[1]Mean ± SE.
[2]Fisher's Exact Test.
[3]Mean reciprocal of titer (35% binding) at time of first breeding.

As illustrated in Table 5, weight at breeding was not affected by treatment. However, immunization against SRIF significantly (P<0.05) increased litter size when compared to the control animals. Piglet weight at birth and litter weight at birth were not significantly different.

TABLE 5

The Influence of Immunization Against SRIF on Reproductive Performance of Gilts

| | Control | SRIF-immune | Probability |
|---|---|---|---|
| Number of Observations | 11 | 11 | |
| Weight at breeding (kg) | 99.0 ± 1.5[1] | 97.1 ± 2.5 | 0.55[2] |
| Litter size | 8.5 ± 0.56[A] | 10.4 ± 0.61[B] | 0.042 |
| Piglet weight at birth | 1.47 ± 0.05 | 1.41 ± 0.04 | 0.337 |
| Litter weight at birth (kg) | 11.7 ± 0.75 | 12.8 ± 0.65 | 0.285 |
| Anti-SRIF-14 titer[3] | 0 | 3800 | |

[1]Mean ± SE; Means in the same row with different superscripts are different (P < 0.05).
[2]Fisher's Exact Test.
[3]Mean reciprocal of titer (35% binding) at time of first breeding.

EXAMPLE 8

Studies on the Effect of SRIF Immunization on Breeding Hens

A. Production of Recombinant VP6

To produce the recombinant VP6, gene 6 of bovine rotavirus C486 was first cloned in the PstI site of pBR322. The resulting clone was digested with AhaIII and HpaIII and subcloned into the SmaI site of pAC373. After transfection into *Escherichia coli*, plasmids in recombinant ampicillin resistant colonies were screened by restriction enzyme analysis for inserts in the correct transcriptional orientation. To transfer gene 6 cDNA from the pAC373 vector to the *Autographa californica* nuclear polyhedrosis virus (AcNPV) DNA, *Spodoptera frugiperda* cells were cotransfected with wild-type AcNPV DNA using the calcium phosphate precipitation procedure previously described (Smith et al., 1983). Following incubation at 27° C. for 7 hrs, the medium was removed and the cells observed with an inverted microscope for signs of infection. The extracellular virus was harvested at 5 days post-infection and plaqued on *Spodoptera frugiperda* cell monolayers. Recombinants were selected by identifying occlusion negative plaques with an inverted microscope. Positive plaques were further grown in microtiter dishes and nucleic acid dot blots of infected cells in these dishes were performed to verify the presence of gene 6. Plaque purification of positive supernatants from microtiter wells was performed and the virus from these plaques was used to propagate virus stocks.

To isolate VP6 from infected cells, the cells were first lysed with a buffer containing 1% NP40, 0.137 M NaCl, 1 mM $CaCl_2$, 0.5 mM $MgCl_2$ and 0.1 mg/ml aprotinin. The lysate was then dialyzed in 0.01M citrate buffer, pH 4.0, for 48 hrs during which time a precipitate (reassembled VP6) formed in the dialysis bag. The precipitate was then collected by centrifugation, then treated with 0.05M EDTA, pH 5.0, for 1 hour and recentrifuged. The resulting pellet contained purified VP6 reassembled spheres.

Rotavirus C486 is publicly available from the American Type Culture Collection (ATCC), 12301 Parklawn Dr., Rockville, Md. 20852, USA, where it was deposited under Accession No. VR-917 on Apr. 15, 1981. The pAC373 vector containing the rotavirus gene 6 cDNA was designated pAC373BRV6 and deposited with the ATCC on Aug. 31, 1987 under Accession No. 40362, where it will be maintained under the terms of the Budapest Treaty.

B. Coupling VP6 to SRIF

Recombinant VP6 spheres as produced above were coupled to SRIF by carbodiimide linkage at a coupling ratio of 1 SRIF:1 VP6 monomer in the following manner. 5 mg of cyclic SRIF (Bachem) was dissolved in 0.5 ml of 10 mM phosphate buffer, pH 6.5. 5 mg of VP6 spheres were dissolved in 2.5 ml of the same buffer. 2 mg of EDAC (water soluble carbodiimide) was added to the VP6 solution and mixed for 2 minutes. The SRIF solution was then added, mixed thoroughly, and incubated at 4° C. overnight with continuous rocking on an agitator platform. The sample was dialyzed against double distilled water with 3 changes for 1 hour at room temperature. The product precipitated but could be evenly dispersed with shaking.

C. Immunization of Hens with SRIF-VP6

Hyline CV16 White Leghorn hens were used in a preliminary experiment to study the effects of SRIF immunization on reproductive efficiency. Hens that were producing eggs were divided into 4 groups of 10 birds each designated:

1) Uninjected control (UC);
2) Saline injected control (SC);
3) 25 μg SRIF per ml (25S);
4) 100 μg SRIF per ml (100S).

Hens from each group were inseminated with pooled semen derived from White Leghorn roosters. Hens and eggs were monitored prior to immunization. Hens were then immunized using from 0.5 to 2.0 ml, more preferably 1 ml, of the SRIF-VP6 complex. The hens were monitored and plasma antibody titers for SRIF determined. Hens were boosted using from 0.5 to 2.0 ml of the SRIF-VP6 carrier complex. Plasma antibody titers to SRIF were determined and hens and eggs monitored. Hens were then inseminated with pooled White Leghorn rooster semen and eggs collected for antibody analysis. Eggs were monitored, counted and egg quality determined. Chicks hatching from the eggs were weighed and growth rate monitored. No significant difference in egg numbers was seen when test groups were compared with the control hens. However, significant quantities of antibodies to SRIF were found in the eggs of the test groups indicating that the immunization was successful. The SRIF immunity was found to be present in the newly hatched chick. The results observed may be attributable to the fact that this breed of hen is already very fertile.

EXAMPLE 9

Effects of SRIF on Granulosa and Luteal Cells

A. Granulosa cells were isolated from mature ovarian follicles from swine by a gentle scraping of the inner follicular membrane, as described in Rajkumar et al., 1989. The cells were incubated either in the presence or absence of 2 μg luteinizing hormone (LH) or 25 μM forskolin (FK). Titrated amounts of SRIF as indicated in FIG. 3, were added to the cells in incubation tubes 5 minutes prior to the addition of LH or FK. The incubations were carried out for 1 hour at 37° C. in the presence of phosphodiesterase inhibitor. The incubations were terminated by boiling the samples for 15 minutes. The samples were then centrifuged and the cAMP in the supernatant measured by RIA, as described by Brooker et al., 1979.

As can be seen in FIG. 3, SRIF inhibited FK stimulated cAMP and to some extent LH stimulated cAMP. In agreement with other literature reports regarding pituitary cells, SRIF did not inhibit the basal cAMP activity. The effect appeared only when cAMP levels were stimulated 20–30% over basal levels.

B. Granulosa cells were also incubated with FK either in the presence or absence of SRIF, and the presence or absence of anti-SRIF. SRIF was added to the incubations 5 minutes before the addition of FK. For the samples with anti-SRIF, the SRIF was preincubated for 1 hour with a predetermined quantity of antibody sufficient to neutralize SRIF activity. Antibodies were prepared as described in Example 3.

As can be seen in FIG. 4, the inhibition of cAMP activity in the presence of SRIF is removed in some cases, for example, in the presence of SRIF alone, or SRIF plus FK when treated with SRIF specific antisera, returning the suppressed cAMP to control levels.

C. Luteal cells were isolated as described above with respect to granulosa cells and SRIF titration performed as described in Example 9A.

As can be seen in FIG. 5, basal cAMP activity in luteal cells was also affected by SRIF at very low doses.

These results suggest that immunization with SRIF elicits an immune response which in turn prevents suppression of cAMP activity and thus enhances reproductive efficiency.

EXAMPLE 10

Increased PMN Activity Attributed to Polyclonal Antisera to Somatostatin-like or Somatostatin-related Peptides The immunogenic preparation from Example 1 was injected subcutaneously into sheep at two sites in the neck region. Dosages were in the range of 0.25 mg to 0.50 mg SRIF-14 per animal. Booster immunizations, using the preparation described in Example 6, at the same doses as initial injection, were given at 3 weeks and then at 4 week intervals, or as necessary. Animals always received a booster vaccination 10 days prior to breeding and again two weeks prior to lambing (estimated). Titers against SRIF in the ewes covered a wide range from $10^4$ to $3 \times 10^5$.

For the purpose of this example, blood samples were obtained from SRIF-14 immunized or a placebo group that were given only the carrier protein without SRIF-14, at $-21$, $-14$ and $-7$ days prior to lambing, at lambing, and at $+3$, $+7$ and $+14$ days post-lambing. Peripheral blood was collected from the jugular vein, into sodium citrate. The citrated blood was centrifuged and the buffy-coat layer removed. The PMN population was isolated from the erythrocyte pellet by hypertonic lysis of the erythrocytes as described by Ohmann et al., 1984.

The functional activity of the cells was measured by superoxide anion generation using the method described by Johnson et al., 1978, and modified by Ohmann et al., 1984. Briefly, superoxide anion generation and release was measured by the reduction of nitroblue tetrazolium (NBT). Approximately $10^6$ cells in 0.05% NBT were activated with zymosan (2.5 mg) by incubating for 30 min at 37° C. The reaction was stopped, the cells pelleted and the reduction of NBT measured spectrophotometrically at 572 nm.

Figure 6:
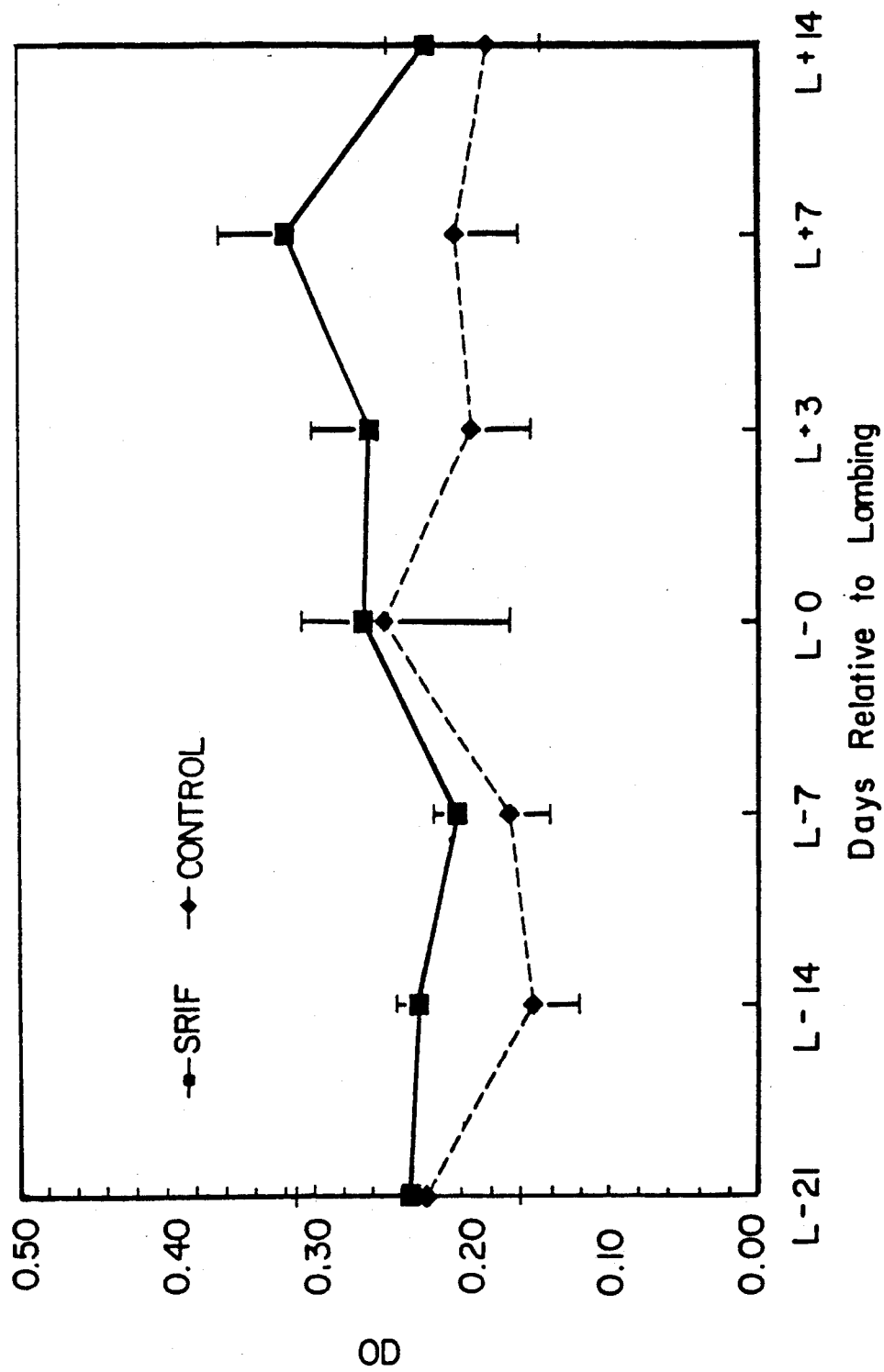
FIG. 6 shows the effect of SRIF on PMN activity in samples obtained from immunized sheep.

PMN activity of SRIF-immunized animals was increased significantly above the levels observed in the controls (see FIG. 6). The increased activity peaked 7 days post-parturition, coinciding with the period of immunosuppression normally observed in animals around the time of parturition.

Thus, compositions and methods for enhancing the reproductive performance and immunological function in vertebrates have been described. Although preferred embodiments of the subject invention have been described in some detail, it is understood that obvious variations can be made without departing from the spirit and the scope of the invention as defined by the appended claims.

References

Arimura, A., et al., 1976a. *Endocrinology* 98:1069–1072.
Arimura, A., et al., 1976b. *Endocrinology* 98:540–543.
Bielefeldt, Ohmann, et al., 1984. *J. Interferon Res.* 4:249–263.
Bielefeldt, Ohmann, et al., 1984. *Inflamm.* 8:251–275.
Blalock, et al., 1985. *J. Immunol.* 135:858s–861s.
Brazeau, P., 1986. *Amer. J. Med.* 81 (Suppl 6B):8–13.
Brooker, et al. 1979. *In Advances in Cyclic Nucleotide Research*, Brooker, Greengard, and Robyson, eds. Vol. 10, p. 1.
Deligeorgis, S. G., et al., 1988. *Animal Production* 46:304.
Feng, P., et al., 1987. *Life Sciences* 120:1121–1126.
Ferland, L., et al., 1976. *Biochem. Biophys. Res. Commun.* 68:149.
Froesch, E. R., et al., 1976. *Proc. Natl. Acad. Sci.* (USA) 73:2904.
Hafs, et al., 1977. *J. Anim. Sci.* 44(6):1061–1066.
Harlow, et al. 1988. *Antibodies a Laboratory Manual*, Cold Spring Harbor.
Hoefler, W. C., et al., 1988. *Theriogenology* 29(2):519–524.
Johnson, et al., 1978. *J. Exp. Med.* 148:115–127.
Johnson, et al., 1985. *J. Immunol.* 135:7735–7755.
Kapikan et al., 1988. *In Virology.* B. N. Fields et al., eds., pp. 863–906.
Kirkwood, R. N., et al., 1988a. *Domestic Animal Endocrinology* 5:317.
Kirkwood, R. N., et al., 1988b. *Can. J. Animal Sci.* 68:1097–1103.
Laarveld, B., et al., 1986. *Can. J. Animal Sci.* 66:77.
Liebow, C., et al., 1989. *Proc. Natl. Acad. Sci.* (USA) 86:2003–2007.
Moreau, U. P., et al., 1987. *Life Sciences* 40:419–437.
Mori, T., et al., 1984. *Acta Endocrinol.* (Copenhagen) 106:254–259.
Mori, T., et al., 1985. *Acta Endocrinol.* (Copenhagen) 100:408–412.
Patel, Y. C., 1984. "Radioimmunoassay of SRIF-related Peptides" in *Methods in Diabetes Research*, J. Larner and S. Pohl, eds., vol. 1, John Wiley and Sons, Inc., New York, p. 307.
Payan, et al., 1984. *Cell Immunol.* 94:433–441.
Rajkumar, K., 1989, *J. Endocrinology* 122:557–564.
Rawlings, N. C., et al., 1987. *J. Animal Sci.* 65:651.
Reichlin, S., 1983. *New Eng. J. of Med.* 309(24):1495–1501 (part one) and 309(25):1556–1563 (part two).
Schalch, D. S., et al., 1979. *Endocrinology* 104:1143.
Schusdziarra, V., 1985. In *Somatostatin*. Y. C. Patel and G. S. Tannenbaum, eds. Plenum Publishing Corp., New York, N.Y. Smith et al., 1983. *J. Virol.* 46:584–593.
Spencer, G. S. G., 1986. "Hormonal Manipulation of Animal Production by Immunoneutralization" in *Control and Manipulation of Animal Growth*, Editors P. J. Buttery et al., Butterworths, Boston.
Spencer, G. S. G., et al., 1983. *Livestock Prod. Sci.* 10:25–37.
Stanisz, et al., 1986. J. Immunol. 136:152–164.
Stryer, L., 1981. *Biochemistry*, 2nd. ed. San Francisco: W. H. Freeman and Co., page 845.
Tannenbaum, G. S., et al., 1978. *Endocrinology* 102:1909–1914.
Tilly, J. L., et al., 1990. *Endocrinology* 126:2079–2087.
Varner, M. A., et al., 1980. *Endocrinology* 106:1027.
Vittoria, A., et al., 1989. *Anat. Histol. Embryol.* 136–142.
Veldhuis, J. D., et al., 1985. *Biochem. Biophys. Res. Commun.* 130:234–240.
Watkins, W. B., et al., 1980. *J. Clin. Endocrinol. Metab.* 50:969–971.
Yousefi, S., et al., 1990. *Proc. Soc. Exp. Biol. Med.* 194:114–118.

We claim:

1. A composition comprising a pharmaceutically acceptable vehicle, an SRIF-related peptide capable of cross-reacting with antisera raised against SRIF-14, said SRIF-related peptide liked to ovalbumin, and an adjuvant comprising Al(OH)$_3$.

2. A method for enhancing the reproductive efficiency in a vertebrate subject by inducing an immunologic reaction, said method comprising administering to said vertebrate subject a therapeutically effective amount of a composition comprising a pharmaceutically acceptable vehicle and an SRIF-related peptide capable of cross-reacting with antisera raised against SRIF-14, linked to a carrier.

3. The method of claim 2 wherein said administering is done intramuscularly, orally, or intranasally.

4. The method of claim 2 wherein from about 1 µg/kg body weight to about 50 µg/kg body weight SRIF-14 are present in said composition.

5. The method of claim 2 wherein said administering is done prior to breeding said vertebrate.

6. A method for enhancing the immunological function in a vertebrate subject by inducing an immunologic reaction, said method comprising administering to said vertebrate subject a therapeutically effective amount of a composition comprising a pharmaceutically acceptable vehicle and an SRIF-related peptide capable of cross-reacting with antisera raised against SRIF-14, linked to a carrier.

7. A method for modulating SRIF activity in a vertebrate subject by inducing an immunologic reaction, said method comprising administering to said vertebrate subject a therapeutically effective amount of a composition comprising a pharmaceutically acceptable vehicle and an SRIF-related peptide capable of cross-reacting with antisera raised against SRIF-14, linked to a carrier.

8. A method for enhancing phagocytic cell function in a vertebrate subject by inducing an immunologic reaction, said method comprising administering to said vertebrate subject a therapeutically effective amount of a composition comprising a pharmaceutically acceptable vehicle and an SRIF-related peptide capable of cross-reacting with antisera raised against SRIF-14, linked to a carrier.

9. The method of claim 4 wherein said carrier is ovalbumin and said composition further comprises $Al(OH)_3$ as an adjuvant.

10. The method of claim 6 wherein said SRIF-related peptide is SRIF-14.

11. The method of claim 10 wherein said carrier is ovalbumin and said composition further comprises $Al(OH)_3$ as an adjuvant.

12. The method of claim 7 wherein said SRIF-related peptide is SRIF-14.

13. The method of claim 12 wherein said carrier is ovalbumin and said composition further comprises $Al(OH)_3$ as an adjuvant.

14. The method of claim 8 wherein said SRIF-related peptide is SRIF-14.

15. The method of claim 14 wherein said carrier is ovalbumin and said composition further comprises $Al(OH)_3$ as an adjuvant.

* * * * *